(12) United States Patent
Freeman et al.

(10) Patent No.: US 8,012,159 B2
(45) Date of Patent: Sep. 6, 2011

(54) PUTAMEN GRID

(75) Inventors: Thomas B. Freeman, Tampa, FL (US);
James P. O'Connor, Billerica, MA (US)

(73) Assignee: University of South Florida, Tampa, FL (US)

(*) Notice: Subject to any disclaimer, the term of this patent is extended or adjusted under 35 U.S.C. 154(b) by 1504 days.

(21) Appl. No.: 10/908,648

(22) Filed: May 20, 2005

(65) Prior Publication Data
US 2006/0009788 A1 Jan. 12, 2006

Related U.S. Application Data

(63) Continuation of application No. PCT/US03/37519, filed on Nov. 20, 2003.

(60) Provisional application No. 60/319,715, filed on Nov. 20, 2002.

(51) Int. Cl.
*A61B 19/00* (2006.01)
(52) U.S. Cl. ........................................ 606/130
(58) Field of Classification Search .............. 606/130; 604/116, 117, 164.04, 174; 600/7
See application file for complete search history.

(56) References Cited

U.S. PATENT DOCUMENTS

| | | | | |
|---|---|---|---|---|
| 4,883,053 A * | 11/1989 | Simon | | 606/130 |
| 5,019,037 A * | 5/1991 | Wang et al. | | 604/23 |
| 5,196,019 A * | 3/1993 | Davis et al. | | 606/130 |
| 5,590,655 A * | 1/1997 | Hussman | | 600/426 |
| 5,626,829 A * | 5/1997 | Koutrouvelis | | 424/1.11 |
| 5,868,757 A * | 2/1999 | Koutrouvelis | | 606/130 |
| 5,871,448 A * | 2/1999 | Ellard | | 600/459 |
| 5,931,786 A * | 8/1999 | Whitmore et al. | | 600/459 |
| 5,957,935 A * | 9/1999 | Brown et al. | | 606/130 |
| 6,500,109 B2 * | 12/2002 | Tokita et al. | | 600/7 |
| 6,508,786 B2 * | 1/2003 | Huitema et al. | | 604/116 |
| 6,551,275 B2 * | 4/2003 | Fontayne et al. | | 604/116 |
| 6,554,759 B2 * | 4/2003 | Fontayne et al. | | 600/7 |
| 6,579,262 B1 * | 6/2003 | Mick et al. | | 604/116 |
| 2003/0130575 A1 * | 7/2003 | Desai | | 600/417 |
| 2003/0139642 A1 * | 7/2003 | Hogendijk et al. | | 600/7 |
| 2004/0220444 A1 * | 11/2004 | Hogendijk et al. | | 600/7 |

OTHER PUBLICATIONS

C.W. Olanow et al., Fetal Nigral Transplantation as a Therapy for Parkinson's Disease, TINS vol. 19; No. 3, 1996, p. 102-108.
Thomas B. Freeman et al., Bilateral Fetal Nigral Transplantation into the Postcommissural Putamen in Parkinson's Disease, Annals of Neurology, vol. 38, No. 3, 1995, p. 379-386.

(Continued)

*Primary Examiner* — Darwin P Erezo
(74) *Attorney, Agent, or Firm* — Robert Varkonyi; Smith & Hopen, P.A.

(57) ABSTRACT

The present invention makes a grid array, for use in the transplantation of materials into the brain, in the shape of a predetermined structure, such as the putamen, based on anatomic analysis the structure. Alternatively, a smaller grid array is used which only includes the putamen target and not the caudate target, and also has two windows within the grid array. Because of the smaller size of this grid array as well as the two cutouts in the middle, it is possible for the first time to observe the brain as the needle enters the brain through the grid array. The previous solid and larger grid array made the passage of the needle into the brain a blind maneuver. Therefore if there was cortical bleeding at the time of needle insertion, it would not be known until after the transplant was done.

16 Claims, 5 Drawing Sheets

OTHER PUBLICATIONS

Thomas B. Freeman et al., Human Fetal Tissue Transplantation, Neurosurgical Treatment of Movement Disorders, 1998, Chapter 13, p. 177-192.

Robert A. Hauser et al., Long-Term Evaluation of Bilateral Fetal Nigral Transplantation on Parkinson Disease, Archives of Neurology, vol. 56 (2), 1999, p. 179-187.

C. Warren Olanow, A Double-Blind Controlled Trail of Bilateral Fetal Nigral Transplantation on Parkinson's Disease, Annals of Neurology, vol. 54, No. 3, 2003, p. 403-414.

Ivar Mendez et al., A Neural Transplantation Cannula and Microinjector System: Experimental and Clinical Experience, Neurosurgical Focus 7 (3), Article 2, 1999, p. 1-9.

R. A. Hauser et al., Fifteenth Annual Symposia Abstracts., Movement Disorders, vol. 16, No. 5, 2001, p. 983-984.

Rae Bakay et al., Sterotaxic Intrastriatal Implantation of Retinal Pigment Epithelial Cells Attached to Microcarri . . . , 2002.

RL Watts et al., Stereotaxic Implantation of Retinal Pigment Epithelial Cells Attached to Microcarriers in Advanced Parkinson Disease Patients . . . , 2001.

RL Watts et al., Stereotaxic Intrastriatal Implantation of Retinal Pigment Epithelial Cells Attached to Microcarriers in Advanced Parkinson Disease Patients . . . , 2002.

RL Watts et al., Stereotaxic Intrastriatal Implantation of Retinal Pigment Epithelial Cells Attached to Microcarriers in Advanced Parkinson Disease Patients . . . , 2003.

* cited by examiner

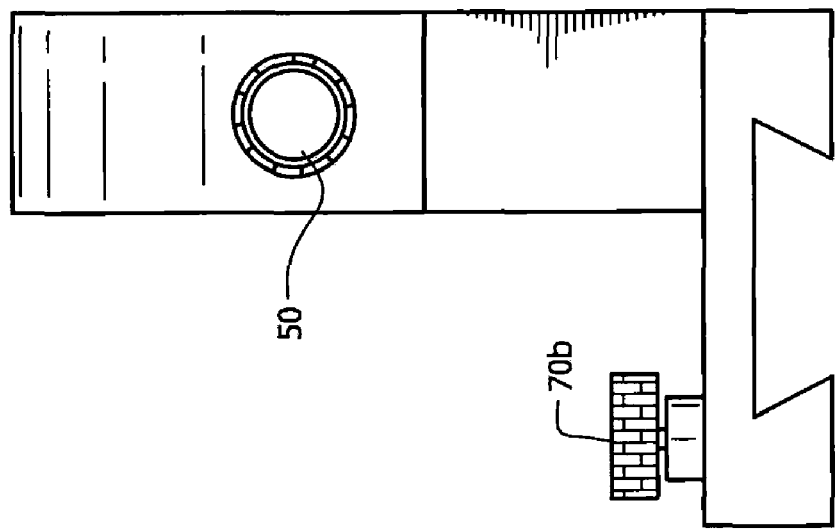
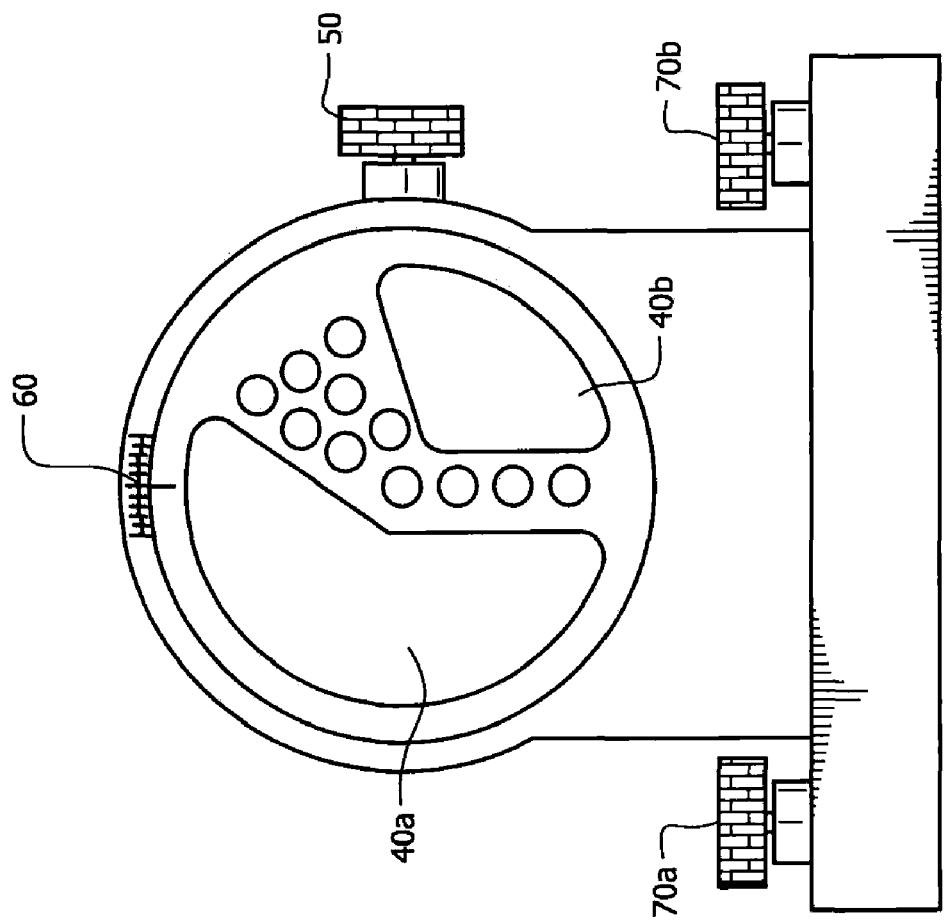

PUTAMEN GRID

CROSS REFERENCE TO RELATED DISCLOSURES

This application is a continuation of International Patent Application No. PCT/US2003/037519, filed on Jan. 8, 2003, which claims the benefit of U.S. Provisional Patent Application Ser. No. 60/319,715 filed Nov. 20, 2002.

BACKGROUND OF THE INVENTION

Field of the Invention

This invention relates to a grid array for neurological surgery.

SUMMARY OF INVENTION

Neural transplantation of fetal tissue has long been studied as means for treating certain neurological disorders such as Parkinson's disease (PD) and Huntington's disease. PD is primarily caused by the loss of nigrostriatal dopaminergic neurons. Symptoms can often be improved with dopamine replacement therapy. The dopamine neurons do not possess the same highly specific, and somatotopically organized information that is demonstrated in other areas of the brain. The target area (striatum) is particularly suitable for transplantation because it is comparatively small. Fetal tissue grafted into this area can survive, reinnervate the brain, and improve behavioral deficits resulting from the onset of PD. It is sometimes necessary to inject deposits of embryonic nigral cells at 5-mm intervals throughout the target areas 3-dimensional configuration.

To this end a grid array with holes every 5 mm, similar to a honeycomb, is utilized so that multiple needle tracts can be made 5 mm apart. The prior art describes a similar grid array with needles every 4 mm in a straight line so that they could transplant six to eight needle tracts in the putamen in a straight line. One embodiment of the present invention makes a grid array in the shape of the putamen, based on anatomic analysis of putamen shape for the human brain. Alternatively, a smaller grid array is used which only includes the putamen target and not the caudate target, and also has two windows within the grid array. Other embodiments of the invention which can be envisioned and are within the scope of this application is the grid array in the shape of any desired area of the brain to which transplantation is desired or surgical procedures. Because of the smaller size of this grid array as well as the two cutouts in the middle, it is possible for the first time to directly observe the brain as the needle enters the brain through the grid array. The previous solid and larger grid array made the passage of the needle into the brain a blind maneuver. Therefore if there was cortical bleeding at the time of needle insertion, it would not be known until after the transplant was done. Thus, the grid array of the present invention clearly overcomes any limitations of other grid arrays available to date.

Methods and procedures for tissue transplantation are provided in Neurosurgical Treatment of Movement Disorders, Freeman et al., pages 177-192 (Neurosurgical Topics, American Association of Neurological Surgeons, 1998) which is incorporated herein by reference.

Therefore, the inventive apparatus comprises a neural transplantation alignment apparatus comprising a base, a puck rotatably secured within the base, the puck having a plurality of needle tracts adapted to receive at least one needle, the plurality of needle tracts forming a grid array, at least one viewing cut-out integral to the puck and coincident to the array whereby the user can observe the progress and movement of the needle passing through said needle tracts, wherein the grid array substantially mirrors the shape of the target within the brain, a series holes within the grid which are spaced apart about twice the distance of the radius of the sphere of influence of the material being injected. The grid array is substantially the same size as the target within the brain, and the grid array is capable of being flipped for matching regions of anatomy on opposite sides of the brain. The grid array is attachable to a stereotactic frame.

BRIEF DESCRIPTION OF THE DRAWINGS

FIG. 2 provides a front and lateral elevated view of the puck holder, the puck is shown within the holder.

DETAILED DESCRIPTION OF THE PREFERRED EMBODIMENT

Figure 1:
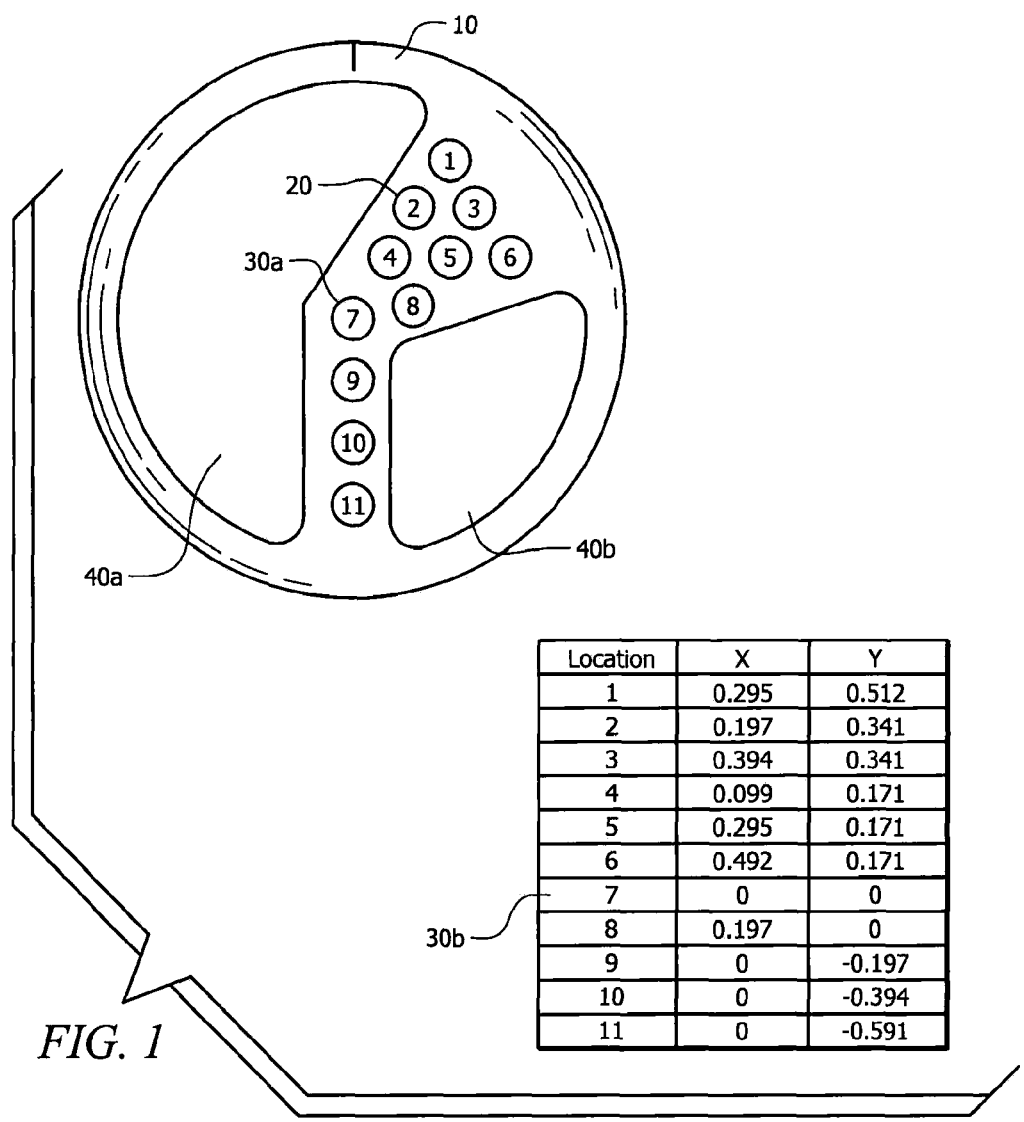
FIG. 1 is a front elevated view of the puck containing the grid array, with a corresponding table showing the coordinates of each needle tract, and viewing windows.
Figure 3:
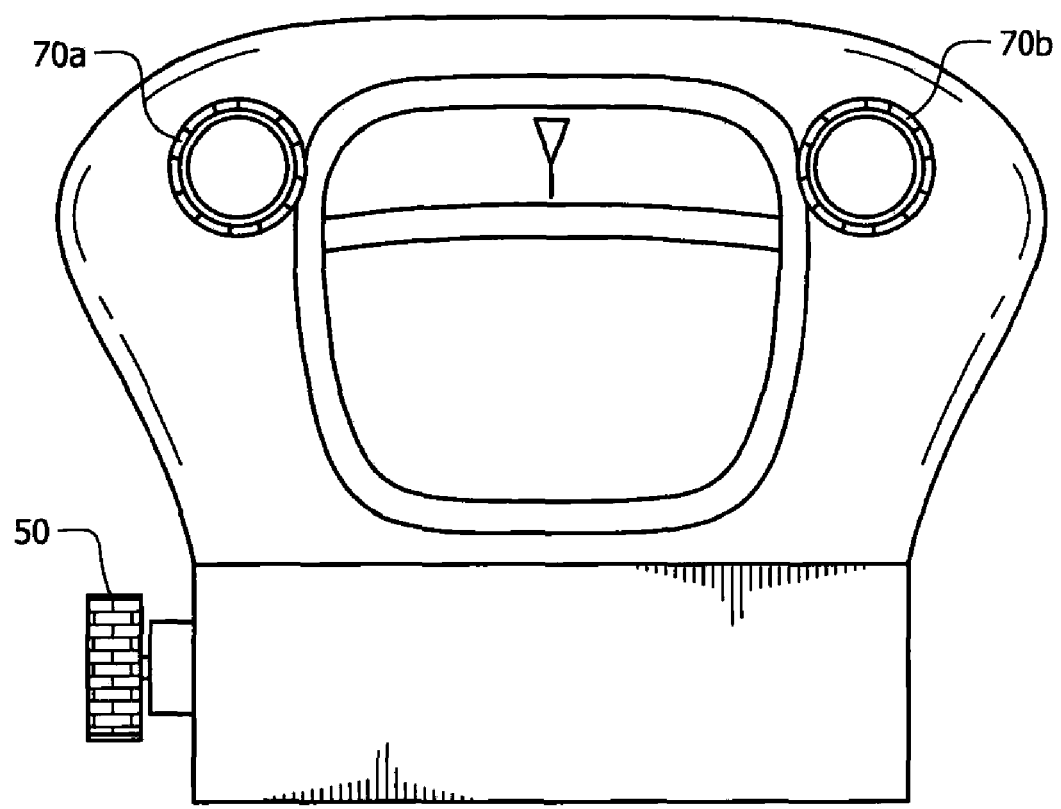
FIG. 3 is a downward view of the puck holder.

Turning to FIG. 1 there are two pucks 10 equipped with a series of holes arranged in the shape of the target structure, here the putamen 20. The shape of the putamen was derived from the human stereotactic atlas by Schaltenbrand and Wahren. All holes, or needle tracts, 20 are either five or seven mm apart. The single stereotactic measurement is made of the "zero point," here shown as "7" 30a (30b indicates the 0,0 coordinate designation) for both the five millimeter grid array and seven millimeter grid array. Surprisingly, a clinically unacceptable margin of error occurs whenever needle tracts exceed a distance of 15 to 20 mm from the "zero point." By keeping the distance of the furthest needle tract under 20 mm from the "zero point" the current invention overcomes this shortcoming in grids discussed in the prior art. It is possible for the user to observe the needle as it is being used by looking through a cut-out 40a-b. FIG. 2 depicts the "puck holder" which attaches directly to the CRW stereotactic frame as a normal platform does. By loosening the screw 50 on the side, the "puck" can be removed. In this way, the grid array can be reversed, and can reflect the shape of the putamen on either the right or the left side. It can also be envisioned that the grid array as described is not to be limited to the CRW sterotactic frame but is described as a means of exemplifying one embodiment of the array. Any stereotactic frame can be optionally used. There are individual degree markings 60 at the top of the "puck" from zero to ten degrees in either direction. There is a single line in the midline. The degree markings are on both sides of the puck. The posterior portion of the grid array (holes labeled 9, 10, 11, etc.) are in a straight line along the midline axis. The grid array can be rotated around the zero point, making these holes parallel to the axis of the tail of the putamen. Two screws 70a-b fasten the puck holder to the stereostatic frame.

Figure 4:
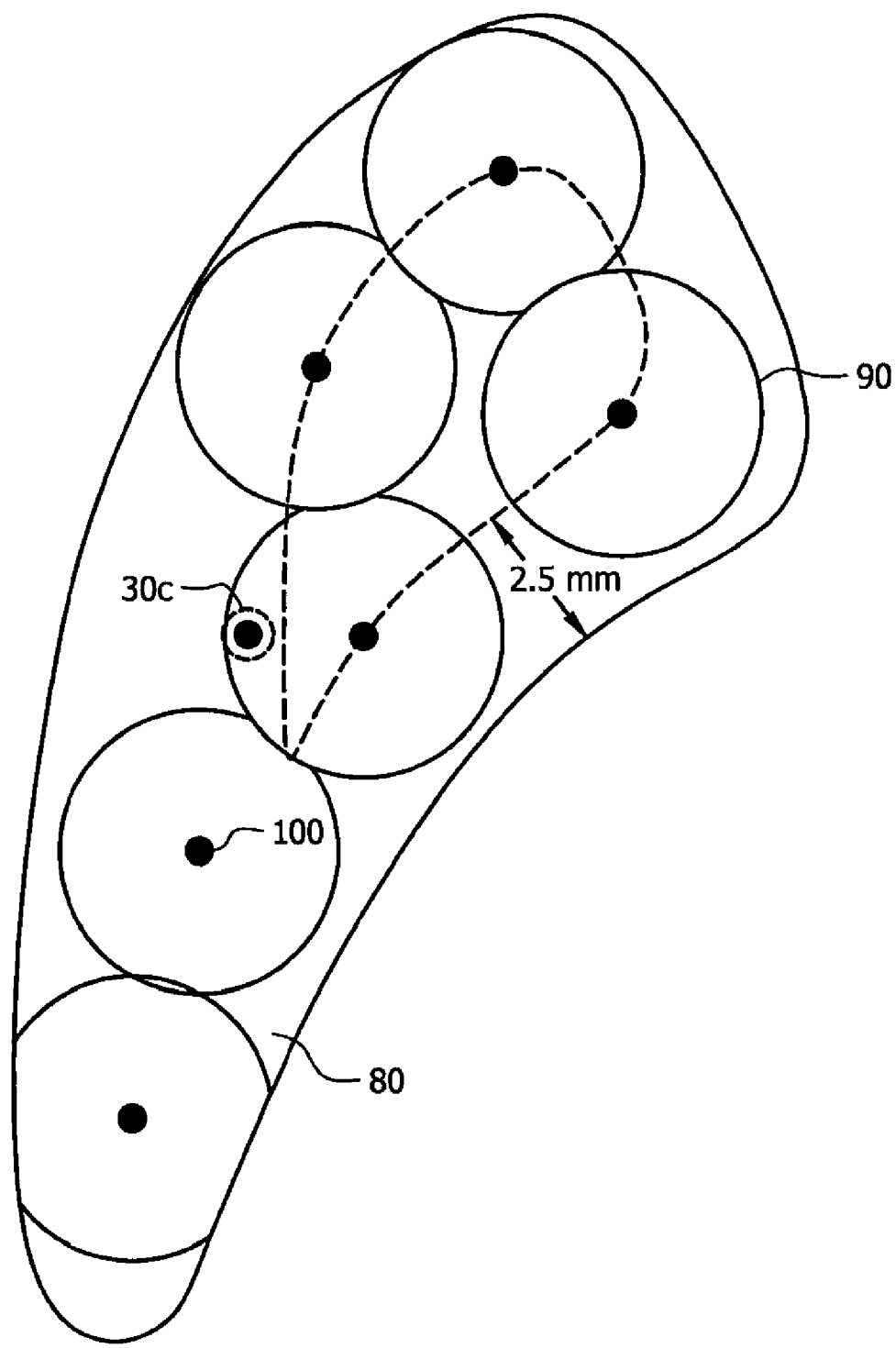
FIG. 4 illustrates the putamen after being injected with a substance that innervates a region of 2.5 mm.

FIG. 4 illustrates the putamen 80 after being injected with a substance that innervates a region of 2.5 mm sphere. Each circle 90 represents the zone affected by the material, while the center of each circle 100 represents the location where the material was injected along the axis of the needle tract. The "zero point" 30c is also indicated.

Figure 5:
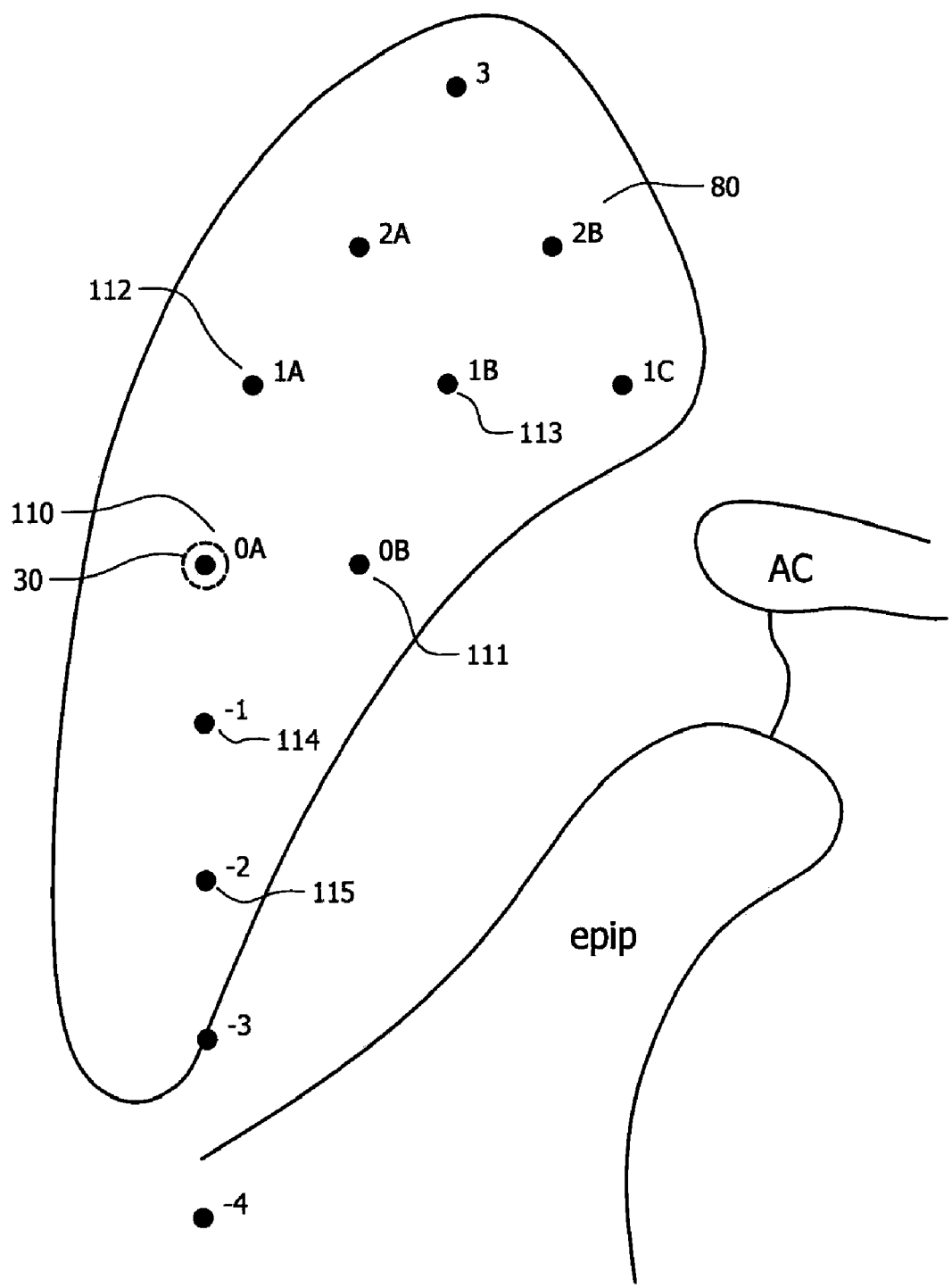
FIG. 5 depicts the 5 mm grid array laid over the putamen.

FIG. 5 depicts the 5 mm grid array laid over the putamen 80. The "zero point" 30 is designated 0-A 110 with the corresponding needle tract 111 along the horizontal axis designated as 0-B. Needle tracts on a superior horizontal axis are designated 1-A 112 and 1-B 113, while needle tracts on a lower horizontal axis are designated -1 114 and -2 115.

By making both pucks for the seven millimeter and five millimeter grid array the same size they can be interchangeable in the "puck holder." Furthermore, it is necessary to make these as small as possible so that the surgeon can see around the lateral aspects of the puck holder into the burr hole. Because of this smaller size, as well as the windows within the grid array, it is possible for the first time to visualize the brain through the grid array as the needle enters the brain.

The size of the grid is substantially the same as the target within the brain. This may be larger than the entry point within the cortex. Therefore, it is possible that a single entry point within the brain cortex could be utilized, and that the shape of the target area within the grid would be reproduced within the brain at the depth of the needle tracts.

The grid array is used for injecting, or transplanting, materials within tissue in the brain. These materials include, but are not limited to, human fetal tissue, porcine dopamine neurons, and human retinal pigment epithelial cells on microcarrier beads. It is also possible to inject gene therapies or other biologic therapies into the brain using the grid array and a sterostatic needle.

A special transplant needle was designed to be used in conjunction with the grid array. The needle has a proximal end the thickness of which is similar to most needles (1.5-2 mm) and a distal end which enters the target area which is thinner (less than 0.9 mm) than most needles. This narrower diameter has been found to correlate with improved transplant survival in vivo. This design provides for minimal trauma in the target area.

There are several stereostatic measurements which must be made in the surgical planning process to determine the location of the "zero point" 30*a*. This is the starting point for injection into the center of the grid array. These measurements comprise; determination of the axis of rotation of the grid array; determination of the anterior and posterior points of injection utilizing the grid array; determination of the needle trajectory to insure the needle trajectory is entirely within the target area; determination of the lowermost point of injection as well as the upper most point of injection; and determination of the cortical entry point, among others.

Using the putamen as an example, the starting point for the measurement for the "zero point" begins 7 mm from the back of the putamen. A measurement is then made 15 mm from that point. The "zero point" lies at this 15 mm point and is 2.5 mm from the lateral aspect of the putamen. Once the zero point is determined the grid can be rotated to be parallel with the axis of the tail of the putamen. This allows for the best fit of all needle tracts. The entry point in the brain is determined so the trajectory of the needle tract is along a the long axis of the target, therefore maximizing deposit material in all three dimensions.

The significance of a single entry point is to minimize the amount of cortical damage by multiple parallel needle tracts. Moreover, the use of a single entry point prevents needle tracts from transgressing a sulcus where more blood vessels are found, which increases the risk of hemorrhage. All tracts can now be within a single sulcus.

Example 1

The needle tracts of the grid array are formed in the shape of the target in the brain, here the putamen. It is important to note that the grid array is not limited to the use on anatomical structures but can also be made in the shape, and used to treat, pathological targets, i.e. a stroke, as well.

Two pucks are implemented, one with needle tracts 5 mm and another with needle tracts 7 mm apart. The distance of the space between the needle tracts is twice that of the radius of the sphere of influence of the material being injected. Therefore, since the sphere of influence of embryonic nigral cells are 2.5 mm and 3.5 mm the needle tracts are spaced at 5 mm and 7 mm respectively.

Because the brain exist in 3-dimensional space a sterostatic needle used in conjunction with the grid array can inject material along the trajectory of the needle as it enters the brain, depositing material at different depths within the tissue. To this end the sterostatic needle is marked with 1 mm or 5 mm indicator lines allowing withdrawal of the needle, through the needle tracts, in a measured fashion. The needle is inserted through the needle tract, into the brain, to the depth of the target. A stopper is utilized while an injection is made. The needle is then withdrawn a certain distance where a subsequent injection is made. This is continued until the entire needle tract within the target region has received injections of the material contained in the stereostatic needle. In this manner the grid array allows transplantation in a 3-dimensional fashion, incorporating not only the xy-plane, but the z-plane as well.

Example 2

The grid array can also be used with one puck in substantially similar fashion as Example 1. Because each puck is circular, removable, and marked on both sides, it is possible to remove the puck and flip it to its opposite side. This creates a mirror image and allows use of the same array on structures on opposite sides of the brain. One grid array therefore works on bilaterally occurring regions of anatomy within the brain.

Example 3

In practice the grid array can be used in the following manner. Prior to surgery patients are placed in a standard resonance imaging (MRI-compatible) stereostatic frame. The implantation site (i.e. the putamen) is then visualized with MRI using fast-spin echo sequencing. Axial images are taken in 3 mm sections from below the putamen to above the caudate. Coronal images are also taken at 3 mm sections from 3 cm anterior to the coronal suture and progress caudally through the putamen. Then implantation sites are determined by the "zero point" in the putamen. This is defined as the halfway point between the putamen's rostral and caudal aspects using the lowest axial section. This single stereotactic measurement forms the basis of all other target sites.

During surgery the sterotactic grid is attached to a stereotactic frame (such as a CRW frame) and aligned so that its axial plane is parallel to the axial plane of the MRI and the longitudinal axis is parallel to the axis of the midline of the brain. This is necessary for the proper placement, coordinates, and angle of the sterostatic needle. A burr hole is created in the skull to accommodate the entry of the transplant, or sterostatic, needle. The needle is positioned so that the superficial needle tract remains entirely within the superior frontal gyrus. The material to be injected is aspirated into the sterostatic needle. The transplant needle is placed into the "zero point" of the putamen.

Each needle tract contains tissue from half the mesencephalon (one substantia nigra). Furthermore, each needle tract consists of four deposits in a given volume of stem cells and are implanted at 5 mm intervals. The needle is left in the tissue following the last deposit in each tract for two minutes to avoid graft withdrawal. Any subsequent needle trajectories use the same burr hole and entry point by angling the grid array. A total of 6 to 8 needle tracts are made on each side when performing a bilateral procedure. In such a case the surgery can be separated into two procedures.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A neural transplantation alignment apparatus comprising:
    a base;
    a needle guide having a puck-like shape rotatably secured within the base, such that the needle guide rotates 360 degrees along the needle guide's circumference;
    the needle guide further having a plurality of needle tracts adapted to receive at least one needle, the plurality of needle tracts forming a grid array, the grid array being focused around a "zero point" forming an axis of rotation for the needle guide, the furthest-most needle tract in the array being no more than 20 mm away from the "zero point";
    at least one viewing cut-out integral to the needle guide and adjacent to the array whereby the user can observe the progress and movement of the needle passing through said needle tracts and into a brain.

2. The neural transplantation alignment apparatus of claim 1 wherein the grid array is configured to substantially mirror the shape of an anatomical structure.

3. The neural transplantation alignment apparatus of claim 2, wherein the anatomical structure is a structure within the brain.

4. The neural transplantation alignment apparatus of claim 3 wherein the anatomical structure is a putamen.

5. The neural transplantation alignment apparatus of claim 1 wherein the needle tracts within the grid are spaced apart about twice the distance of the radius of the sphere of influence of the material being injected.

6. The neural transplantation alignment apparatus of claim 1 wherein the grid array is attached to a stereotactic frame.

7. The neural transplantation alignment apparatus of claim 1 wherein the grid array is configured to be substantially the same size as a target within the brain.

8. The neural transplantation alignment apparatus of claim 1 wherein the grid array is capable of being reversed for mirrored regions of anatomy on opposite sides of the brain.

9. The neural transplantation alignment apparatus of claim 1, further comprising:
    a plurality of individual degree markings disposed on the needle guide;
    wherein the degree markings indicate a zero to ten degree angle of rotation in either direction of a midline.

10. The neural transplantation alignment apparatus of claim 1, further comprising
    a second needle guide having a puck-like shape rotatably secured within the base, such that the needle guide rotates 360 degrees, where the second needle guide has a plurality of needle tracts adapted to receive at least one needle; and
    wherein the plurality of needle tracts in the second puck are spaced apart at different distances than the first puck.

11. The neural transplantation alignment apparatus of claim 1, further comprising
    an injection needle, wherein a plurality of markings are disposed on the needle to indicate depth of insertion of the needle.

12. A neural transplantation alignment apparatus comprising:
    a base;
    a needle guide having a puck-like shape rotatably secured within the base, such that the needle guide rotates 360 degrees along the needle guide's circumference;
    the needle guide further having a plurality of needle tracts adapted to receive at least one needle, the plurality of needle tracts forming a grid array, the grid array being focused around a "zero point" forming an axis of rotation for the needle guide, the furthest-most needle tract in the array being no more than 20 mm away from the "zero point";
    at least one viewing cut-out integral to the needle guide and adjacent to the array whereby the user can observe the progress and movement of the needle passing through said needle tracts and into a brain;
    wherein the grid array is configured to substantially mirror the shape of a target within the brain;
    a series of holes within the grid which are spaced apart about twice the distance of the radius of the sphere of influence of the material being injected;
    wherein the grid array is configured to be substantially the same size as the target within the brain;
    wherein the grid array is capable of being flipped for matching regions of anatomy on opposite sides of the brain;
    wherein the grid array is attached to a stereotactic frame.

13. The neural transplantation alignment apparatus of claim 12, further comprising:
    a plurality of individual degree markings disposed on the needle guide;
    wherein the degree markings indicate a zero to ten degree angle of rotation in either direction of a midline.

14. The neural transplantation alignment apparatus of claim 12, further comprising
    a second needle guide having a puck-like shape rotatably secured within the base, such that the needle guide rotates 360 degrees, where the second needle guide has a plurality of needle tracts adapted to receive at least one needle; and
    wherein the plurality of needle tracts in the second needle guide are spaced apart at different distances than the first needle guide.

15. The neural transplantation alignment apparatus of claim 12, further comprising
    an injection needle, wherein a plurality of markings are disposed on the needle to indicate depth of insertion of the needle.

16. The neural transplantation alignment apparatus of claim 12 wherein the target within the brain is a putamen.

* * * * *